(12) United States Patent
Horzewski et al.

(10) Patent No.: US 7,229,423 B2
(45) Date of Patent: Jun. 12, 2007

(54) SYSTEMS AND METHODS FOR APPLYING AUDIBLE ACOUSTIC ENERGY TO INCREASE TISSUE PERFUSION AND/OR VASODILATION

(75) Inventors: Michael J. Horzewski, San Jose, CA (US); Veijo T. Suorsa, Sunnyvale, CA (US); Todd A. Thompson, San Jose, CA (US)

(73) Assignee: Timi 3 System, Inc, Santa Clara, CA (US)

( * ) Notice: Subject to any disclaimer, the term of this patent is extended or adjusted under 35 U.S.C. 154(b) by 281 days.

(21) Appl. No.: 10/359,040

(22) Filed: Feb. 5, 2003

(65) Prior Publication Data

US 2004/0153009 A1 Aug. 5, 2004

(51) Int. Cl.
*A61H 1/00* (2006.01)
(52) U.S. Cl. .......................... 601/21; 600/443
(58) Field of Classification Search ............... 601/21; 600/437, 443, 25
See application file for complete search history.

(56) References Cited

U.S. PATENT DOCUMENTS

| | | | |
|---|---|---|---|
| 3,985,337 A | 10/1976 | Gripe et al. | |
| 4,563,261 A | 1/1986 | Staab et al. | |
| 4,651,716 A | 3/1987 | Forester et al. | |
| 4,791,915 A | 12/1988 | Barsotti et al. | |
| 4,955,365 A | 9/1990 | Fry et al. | |
| 4,966,131 A | 10/1990 | Houghton et al. | |
| 5,024,829 A | 6/1991 | Berger et al. | |
| 5,159,838 A | 11/1992 | Lynnworth | |
| 5,190,766 A | 3/1993 | Ishihara | |
| 5,230,334 A | 7/1993 | Klopotek et al. | |
| 5,267,223 A | 11/1993 | Flanagan et al. | |
| 5,291,894 A | 3/1994 | Nagy | |
| 5,313,935 A | 5/1994 | Kortenbach et al. | |
| 5,359,993 A | 11/1994 | Slater et al. | |
| 5,394,047 A | 2/1995 | Scharlack et al. | |
| 5,400,267 A | 3/1995 | Denen et al. | |
| 5,413,550 A | 5/1995 | Castel | |
| 5,454,373 A * | 10/1995 | Koger et al. ................ 600/463 |
| 5,520,612 A | 5/1996 | Winder et al. | |
| 5,531,119 A | 7/1996 | Meyers | |
| 5,556,372 A | 9/1996 | Talish et al. | |
| 5,580,575 A | 12/1996 | Unger et al. | |
| 5,626,554 A | 5/1997 | Ryaby et al. | |
| 5,695,460 A | 12/1997 | Siegel et al. | |
| 5,698,531 A | 12/1997 | Nabel et al. | |

(Continued)

FOREIGN PATENT DOCUMENTS

JP 8089549 4/1996

(Continued)

OTHER PUBLICATIONS

Koiwa et al., "The effect of diastolic vibration on the coronary flow rate in the canine heart with ischemia" Journal Cardiovasc Diagn Procedures, 12; p. 110.
Lindblad et al., "Effect of Vibration on a Canine Cutaneous Artery," Am J. Physiol, 250 H519-H523 (1986).
Ljung et al., "Inhibition of Vascular Smooth Muscle Contraction by Vibrations" Abstract Acta Physiol. Scand., 396, Suppl., p. 95 (1973).

(Continued)

*Primary Examiner*—Michael A. Brown
(74) *Attorney, Agent, or Firm*—Ryan, Kromholz & Manion, S.C.

(57) ABSTRACT

Systems and methods apply audible acoustic energy to cause vasodilation and/or to increase tissue perfusion.

35 Claims, 8 Drawing Sheets

U.S. PATENT DOCUMENTS

| | | | |
|---|---|---|---|
| 5,720,304 A | 2/1998 | Omura | |
| 5,725,482 A | 3/1998 | Bishop | |
| 5,762,616 A | 6/1998 | Talish | |
| 5,879,314 A | 3/1999 | Peterson et al. | |
| 5,913,834 A * | 6/1999 | Francais | 600/591 |
| 5,991,355 A | 11/1999 | Dahlke | |
| 6,080,187 A * | 6/2000 | Alt et al. | 607/32 |
| 6,095,979 A * | 8/2000 | Ohtomo | 600/449 |
| 6,126,619 A | 10/2000 | Peterson et al. | |
| 6,200,259 B1 | 3/2001 | March | |
| 6,237,604 B1 | 5/2001 | Burnside et al. | |
| 6,254,573 B1 | 7/2001 | Haim et al. | |
| 6,261,537 B1 | 7/2001 | Klaveness et al. | |
| 6,273,864 B1 | 8/2001 | Duarte et al. | |
| 6,295,330 B1 | 9/2001 | Skog et al. | |
| 6,398,772 B1 | 6/2002 | Bond et al. | |
| 6,432,070 B1 | 8/2002 | Talish et al. | |
| 6,434,539 B1 * | 8/2002 | Woodsum et al. | 706/13 |
| 6,477,426 B1 | 11/2002 | Fenn et al. | |
| 6,511,429 B1 * | 1/2003 | Fatemi et al. | 600/443 |
| 6,577,042 B2 | 6/2003 | Lee et al. | |
| 6,635,017 B1 | 10/2003 | Moehring et al. | |
| 6,682,502 B2 | 1/2004 | Bond et al. | |
| 6,979,812 B2 | 12/2005 | Al-Ali | |
| 7,048,687 B1 | 5/2006 | Reuss et al. | |
| 2002/0082528 A1 | 6/2002 | Friedman et al. | |
| 2003/0157025 A1 | 8/2003 | Unger et al. | |
| 2003/0204141 A1 | 10/2003 | Nock et al. | |
| 2004/0133066 A1* | 7/2004 | Mann et al. | 600/25 |
| 2004/0230252 A1 | 11/2004 | Kullok et al. | |
| 2005/0004460 A1* | 1/2005 | Taylor et al. | 600/437 |

FOREIGN PATENT DOCUMENTS

| | | |
|---|---|---|
| WO | WO 85/03634 | 8/1985 |

OTHER PUBLICATIONS

The "Vitafon Device," Vitafon Company, www. vitafon.net

Zagzebski, "Essentials of Ultrasound Physics," Physics of Diagnostic Ultrasound, p. 5.

Ng, K. et al., "Therapeutic Ultrasound: Its Application in Drug Delivery"; Medicinal Research Reviews, vol. 22, No. 2, 204-223, 2002.

Tachibana, K. et al., "The Use of Ultrasound for Drug Delivery"; Echocardiography, vol. 18, May 2001.

Hull, W. et al., "Heat-Enhanced Transdermal Drug Delivery: A Survey Paper"; The Journal of Applied Research, vol. 2, No. 1, Winter 2002.

International Cancer Research Portfolio ABSTRACT—award funding period Jan. 15, 1999 to Dec. 31, 2002, award code CA076562.

Cho, C.W., et al., "Ultrasound induced mild hyperthermia as a novel approach to increase drug intake in brain microvessel endothelial cells", Pharm Res. Aug. 2002;19(8);1123-9.

Internet article: "Good Vibrations Personal Energiser Pty Ltd.—Vitafon-IR" (Google Web address).

Google Website: "Hearing Pitch or Sound Frequencies—Succeed Through Using your Senses" - "Hearing Pitch or Sound Frequencies" by Ron Kurtus (Mar. 7, 2001).

Google Website: "Frequency Hearing Ranges in Dogs and Other Species" - "How Well Do Dogs and Other Animals Hear" references data from Fay (1988) and Warfield (1973) in a table which lists the human audible frequency range between 64-23 000 Hz, and some animals as high as 150 kHz.

* cited by examiner

SYSTEMS AND METHODS FOR APPLYING AUDIBLE ACOUSTIC ENERGY TO INCREASE TISSUE PERFUSION AND/OR VASODILATION

RELATED APPLICATIONS

This application claims the benefit of co-pending U.S. patent application Ser. No. 10/202,447, filed Jul. 24, 2002, entitled "Systems and Methods for Monitoring and Enabling Use of a Medical Instrument." This application also claims the benefit of co-pending U.S. patent application Ser. No. 09/935,908, filed Aug. 23, 2001, entitled "Systems and Methods for Applying Ultrasonic Energy to the Thoracic Cavity." This application also claims the benefit of co-pending U.S. patent application Ser. No. 09/645,662, filed Aug. 24, 2000, entitled "Systems and Methods for Enhancing Blood Perfusion Using Ultrasound Energy."

FIELD OF THE INVENTION

This invention relates to systems and methods for increasing blood perfusion and/or vasodilation.

BACKGROUND OF THE INVENTION

Vasodilation is a term that describes the increase in the internal diameter of a blood vessel that results from relaxation of smooth muscle within the wall of the vessel. Vasodilation can cause an increase in blood flow, as well as a corresponding decrease in systemic vascular resistance (i.e., reduced blood pressure). Tissue perfusion is a term that generally describes blood flow into the tissues.

Vasodilation has been recognized to be beneficial in the treatment of myocardial infarction, strokes, and vascular diseases.

Maintaining adequate tissue perfusion is recognized to be beneficial during any hypoperfused event, during any coronary syndrome including myocardial infarction, before, during, or after medical intervention (e.g., angioplasty, plastic and reconstructive surgery, maxillofacial surgery, vascular surgery, transplant surgery, or cardiac surgery); or before, during, or after dental procedures, or dermatological test patches and other skin challenges, or before, during, or after an exercise regime; or during wound healing.

The effects of ultrasound energy upon enhanced vasodilation and/or blood perfusion have been observed. However, the conventional use of ultrasound energy in medicine for either diagnostic or therapeutic purposes typically has involved the application of ultrasound energy at frequency ranges—e.g., about 2 MHz to 40 MHz for diagnostic purposes (ultrasound imaging), and about 1 MHz to 3 MHz (physiotherapy or diathermy devices)—and/or with attendant exposure times, that can induce thermal effects due to tissue absorption of ultrasound energy. These thermal mechanisms caused by tissue absorption of ultrasound energy can lead to substantial deep heating of tissue. Often, in typically conventional ultrasound modalities, the thermal mechanisms due to absorption of ultrasound energy in tissue can be intended and beneficial, or at least not detrimental. However, when the principal purpose of the therapy is to create vasodilation and/or sustain adequate tissue perfusion in instances where the body is undergoing, or is about to undergo, or has undergone an event that is or has the potential for challenging patient well being, unintended substantial deep tissue heating effects or other unnecessary physiologic challenges to body tissue or organs should be avoided.

SUMMARY OF THE INVENTION

The invention provides systems and methods for applying audible acoustic energy to affect vasodilation and/or an increase in tissue perfusion. The desired physiologic effects can be achieved without substantial deep heating of tissue.

Other features and advantages of the inventions are set forth in the following specification and attached drawings.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

A system 10 will be described in connection with the therapeutic indication of providing vasodilation and/or increased tissue perfusion by the transcutaneous application of audible acoustic energy. As used herein, the term "audible acoustic energy" means vibrational energy in a range of frequencies between about 20 Hz to no greater than 20 kHz.

The audible acoustic energy is desirably indicated, e.g., for the treatment of myocardial infarction, strokes, and vascular diseases; and/or before, during, or after percutaneous or surgical intervention; and/or before, during, or after dental procedures; and/or before, during, or after dermatological test patches and other skin challenges; and/or before, during, or after prescribed exercise regimes; and/or during wound healing. The system 10 has application for use in diverse regions of the body, e.g., in the thoracic cavity, the abdomen, the arms, the legs, the neck, or the head.

I. System for Providing Noninvasive Vasodilation and/or Tissue Perfusion using Audible Acoustic Energy FIG. 1 schematically shows a compact, portable therapeutic system 10 that makes it possible to treat a person who needs or who is likely to need vasodilation and/or an increase in the flow rate to or perfusion of selected tissues.

The system 10 includes durable and disposable equipment and materials necessary to treat the person at a designated treatment location. In use, the system 10 affects vasodilation and/or increased tissue perfusion by transcutaneously applying audible acoustic energy.

Figure 1:
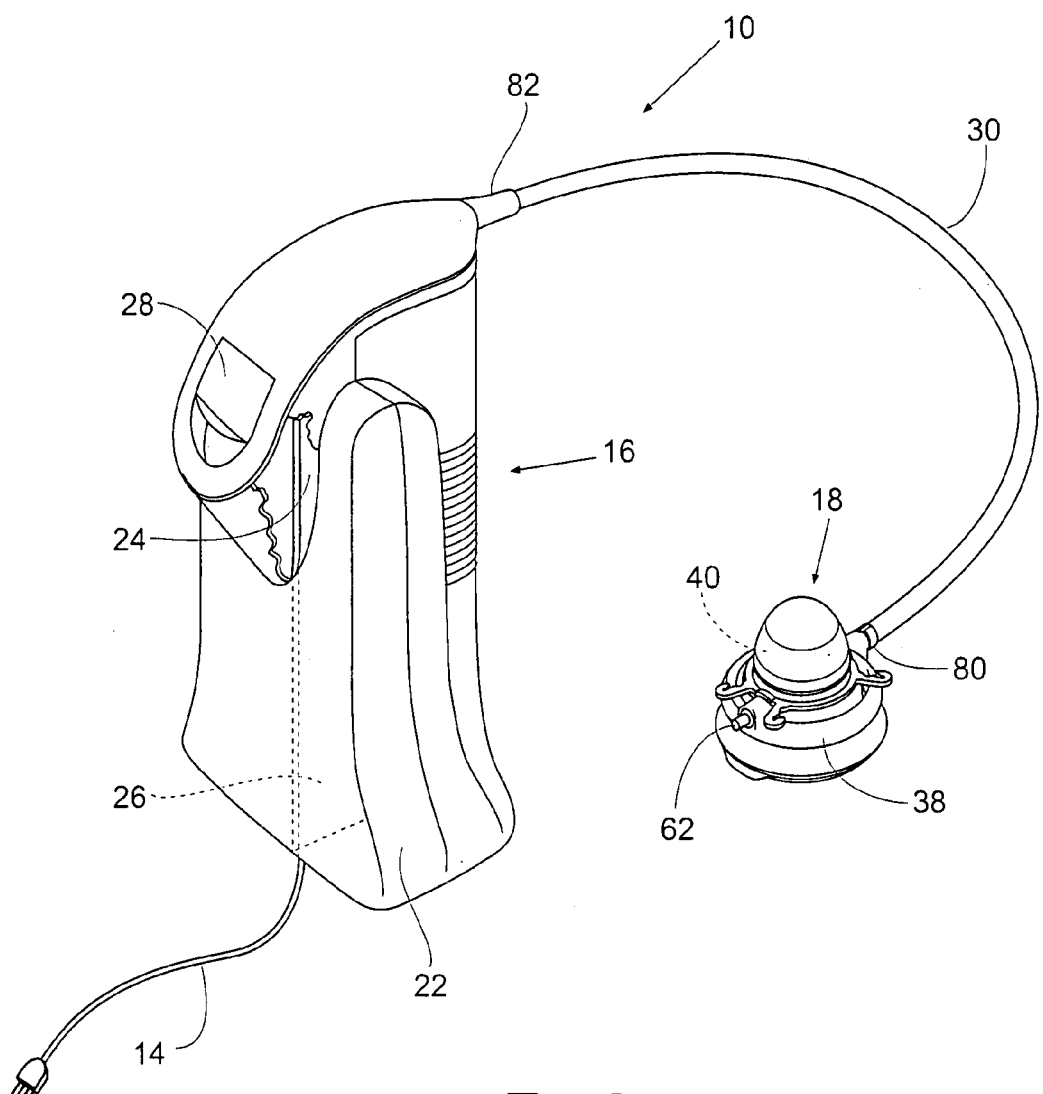
FIG. 1 is a perspective view of a system for transcutaneously applying audible acoustic energy to affect vasodilation and/or increased blood perfusion.
Figure 5:
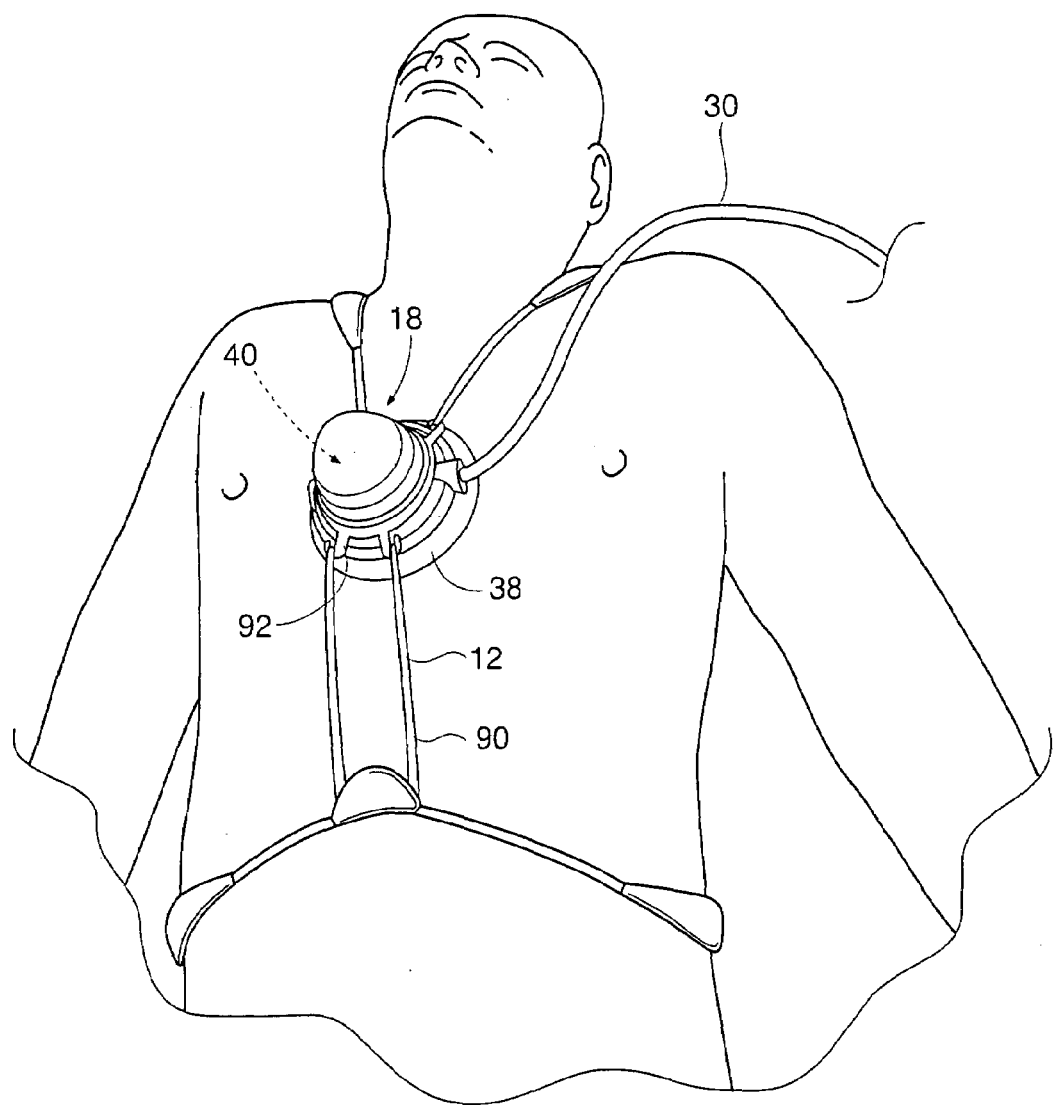
FIG. 5 is a view of the applicator shown in FIG. 2 held by a stabilization assembly in a secure position overlaying the sternum of a patient, to transcutaneously direct acoustic energy, e.g., toward the heart.

As FIG. 1 shows, the system 10 includes at the treatment location an audible acoustic energy generating machine 16. The system 10 also includes at the treatment location at least one audible acoustic energy applicator 18, which is coupled to the machine 16 during use. As FIG. 5 shows, the system 10 also includes an assembly 12 for use with the applicator 18 to stabilize the position of the applicator 18 on a patient for hands-free use. In the illustrated embodiment (see FIG. 5), the applicator 18 is secured against movement on a person's thorax, overlaying the sternum, to direct acoustic energy toward the vasculature of the heart. It should be appreciated that the applicator can be sized and configured for placement on other regions of the body, such as the arms, legs, or head. The applicator can be secured to the patient as well.

The location where treatment occurs can vary. It can be a traditional clinical setting, where support and assistance by one or more medically trained care givers are immediately available to the person, such as inside a hospital, e.g., in an emergency room, catheter lab, operating room, or critical care unit. However, due to the purposeful design of the system 10, the location need not be confined to a traditional clinical setting. The location can comprise a mobile setting, such as an ambulance, helicopter, airplane, or like vehicle used to convey the person to a hospital or another clinical treatment center. The location can even comprise an everyday, public setting, such as on a cruise ship, or at a sports stadium or airport, or a private setting, such as in a person's home, where the effects of vasoconstriction and/or low tissue perfusion can arise.

By purposeful design of durable and disposable equipment, the system 10 can make it possible to initiate treatment of vasoconstriction and/or a reduced tissue perfusion incident in a non-clinical, even mobile location, outside a traditional medical setting. The system thereby makes effective use of the critical time period before the person enters a hospital or another traditional medical treatment center.

The features and operation of the system 10 will now be described in greater detail.

A. The Audible Acoustic Energy Generator

FIG. 1 shows a representative embodiment of the audible acoustic energy generating machine 16. The machine 16 can also be called an "audible acoustic energy generator." The machine 16 is intended to be a durable item capable of long term, maintenance free use.

As shown in FIG. 1, the machine 16 can be variously sized and shaped to present a lightweight and portable unit, presenting a compact footprint suited for transport. The machine 16 can be sized and shaped to be mounted at bedside, or to be placed on a table top or otherwise occupy a relatively small surface area. This allows the machine 16 to travel with the patient within an ambulance, airplane, helicopter, or other transport vehicle where space is at a premium. This also makes possible the placement of the machine 16 in a non-obtrusive way within a private home setting, such as for the treatment of chronic angina.

In the illustrated embodiment, the machine 16 includes a chassis 22, which, for example, can be made of molded plastic or metal or both. The chassis 22 houses a module 24 for generating electric signals. The signals are conveyed to the applicator 18 by an interconnect 30 to be transformed into acoustic energy. A controller 26, also housed within the chassis 22 (but which could be external of the chassis 22, if desired), is coupled to the module 24 to govern the operation of the module 24. Further desirable technical features of the controller 26 will be described later.

The machine 16 also preferably includes an operator interface 28. Using the interface 28, the operator inputs information to the controller 26 to affect the operating mode of the module 24. Through the interface 28, the controller 26 also outputs status information for viewing by the operator. The interface 28 can provide a visual readout, printer output, or an electronic copy of selected information regarding the treatment. The interface 28 is shown as being carried on the chassis 22, but it could be located external of the chassis 22 as well.

The machine 16 includes a power cord 14 for coupling to a conventional electrical outlet, to provide operating power to the machine 16. The machine 16 can also include a battery module (not shown) housed within the chassis 22, which enables use of the machine 16 in the absence or interruption of electrical service. The battery module can comprise rechargeable batteries, which can be built in the chassis 22 or, alternatively, be removed from the chassis 22 for recharge. Likewise, the battery module (or the machine 16 itself) can include a built-in or removable battery recharger. Alternatively, the battery module can comprise disposable batteries, which can be removed for replacement.

Power for the machine 16 can also be supplied by an external battery and/or line power module outside the chassis 22. The battery and/or line power module is releasably coupled at time of use to the components within the chassis 22, e.g., via a power distribution module within the chassis 22.

The provision of battery power for the machine 16 frees the machine 16 from the confines surrounding use of conventional ultrasound equipment, caused by their dependency upon electrical service. This feature makes it possible for the machine 16 to provide a treatment modality that continuously "follows the patient," as the patient is being transported to or inside a transport vehicle, or as the patient is being shuttled between different locations within a treatment facility, e.g., from the emergency room to a catheterization lab or holding area within or outside the emergency room.

In a representative embodiment, the chassis 22 measures about 12 inches×about 8 inches×about 8 inches and weighs about 9 pounds.

B. The Audible Acoustic Energy Applicator

As shown in FIG. 5, the applicator 18 can also be called the "patient interface." The applicator 18 comprises the link between the machine 16 and the treatment site within the thoracic cavity of the person undergoing treatment. The applicator 18 converts electrical signals from the machine 16 to acoustic energy, and further directs the acoustic energy to the targeted treatment site.

Desirably, the applicator 18 is intended to be a disposable item. At least one applicator 18 is coupled to the machine 16 via the interconnect 30 at the beginning a treatment session. The applicator 18 is preferably decoupled from the interconnect 30 (as FIG. 1 shows) and discarded upon the completing the treatment session. However, if desired, the applicator 18 can be designed to accommodate more than a single use.

Figure 2:
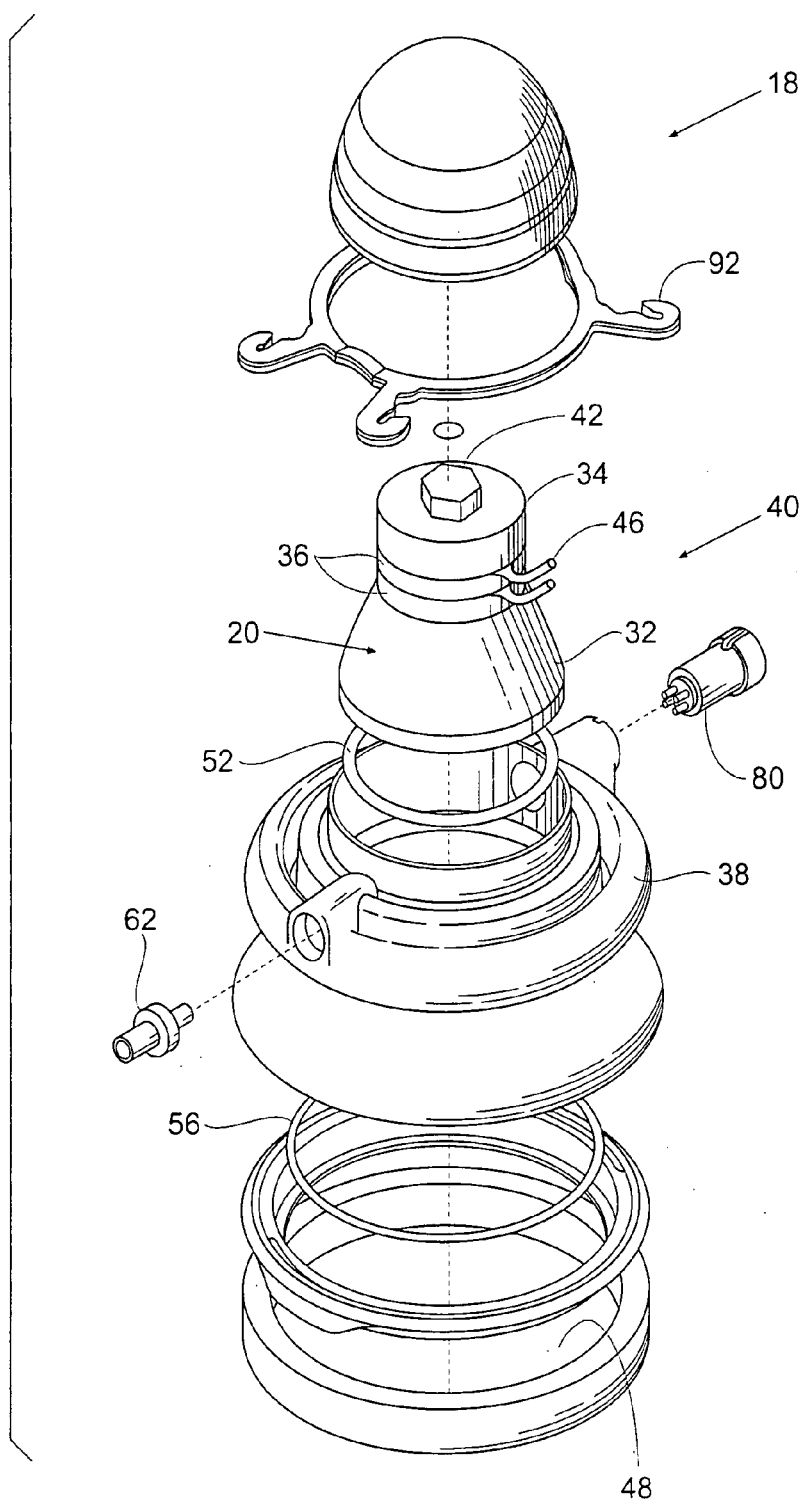
FIG. 2 is an enlarged exploded perspective view of an audible acoustic energy applicator that forms a part of the system shown in FIG. 1.
Figure 3:
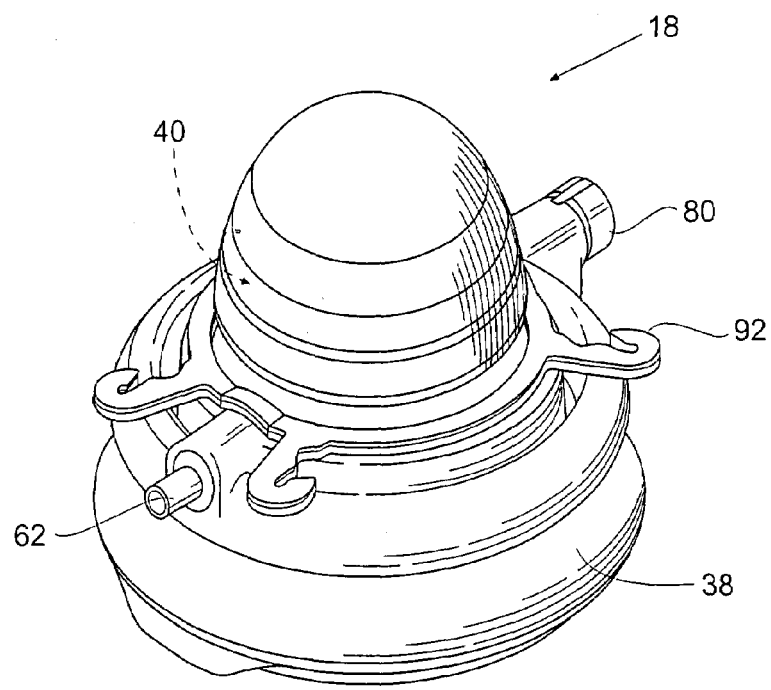
FIG. 3 is an enlarged assembled perspective view of the audible acoustic energy applicator shown in FIG. 2.

As FIGS. 2 and 3 show, the audible acoustic energy applicator 18 includes a shaped metal or plastic body 38 ergonomically sized to be comfortably grasped and manipulated in one hand. The body 38 houses and supports at least one audible acoustic energy transducer 40 (see FIG. 3).

In the illustrated embodiment, the audible acoustic energy transducer 40 comprises an acoustic stack 20. The acoustic stack 20 comprises a front mass piece 32, a back mass piece 34, and one or more piezoelectric elements 36, which are bolted together. The back mass piece 34 comprises an annular ring of material having relatively high acoustic impedance, e.g., steel or stainless steel. "Acoustic impedance" is defined as the product of the density of the material and the speed of sound.

The front mass piece 32 comprises a cone-shaped piece of material having relatively low acoustic impedance, e.g., aluminum or magnesium. The piezoelectric elements 36 are annular rings made of piezoelectric material, e.g., PZT. An internally threaded hole or the like receives a bolt 42 that mechanically biases the acoustic stack 20. A bolt 42 that can be used for this purpose is shown in U.S. Pat. No. 2,930,912. The bolt 42 can extend entirely through the front mass piece 32 or, the bolt 42 can extend through only a portion of the front mass piece 32 (see FIG. 7).

Figure 6:
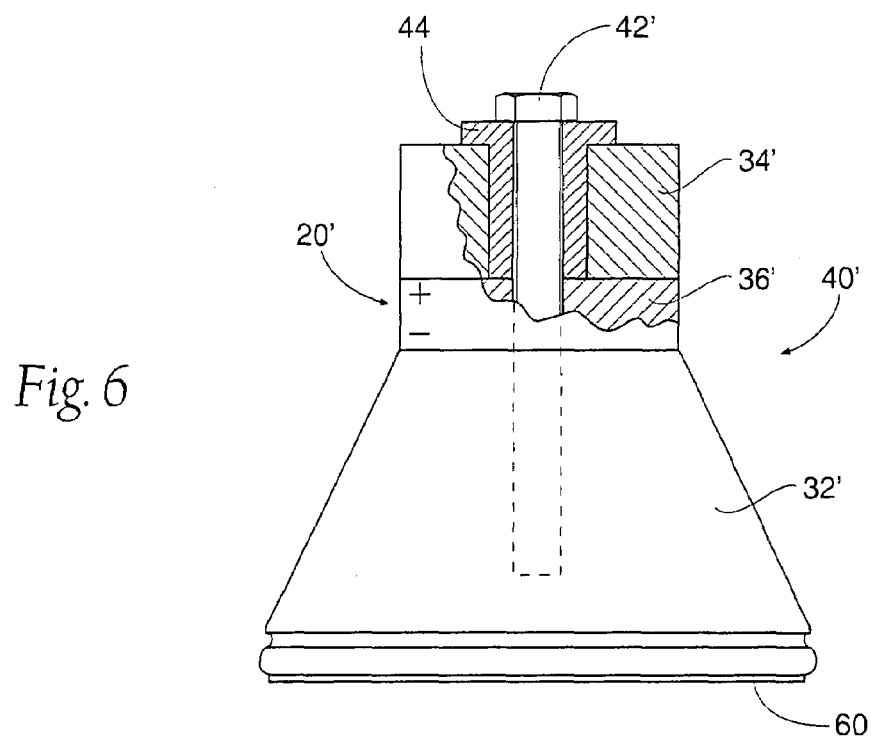
FIG. 6 is a side elevation view, with portions broken away and in section, of an acoustic stack that can be incorporated into the applicator shown in FIG. 2.

In an alternative embodiment (see FIG. 6), the acoustic stack 20' of a transducer 40' can comprise a single piezoelectric element 36' sandwiched between front and back mass pieces 32' and 34'. In this arrangement, the back mass piece 34' is electrically insulated from the front mass piece 32' by, e.g., an insulating sleeve and washer 44.

The piezoelectric element(s) 36/36' have electrodes 46 (see FIG. 2) on major positive and negative flat surfaces. The electrodes 46 electrically connect the acoustic stack 20 of the transducer 40 to the electrical signal generating module 24 of the machine 16. When electrical energy at an appropriate frequency is applied to the electrodes 46, the piezoelectric elements 36/36' convert the electrical energy into mechanical (i.e., acoustic) energy in the form of mechanical vibration.

The mechanical vibration created by the transducer 40/40' is coupled to a patient through a transducer bladder 48, which rests on a skin surface. The bladder 48 defines a bladder chamber 50 (see FIG. 4) between it and the front mass piece 32. The bladder chamber 50 spaces the front mass piece 32 a set distance from the patient's skin. The bladder chamber 50 accommodates a volume of an acoustic coupling media liquid, e.g., liquid, gel, oil, or polymer, that is conductive to acoustic energy, to further cushion the contact between the applicator 18 and the skin. The presence of the acoustic coupling media also makes the acoustic contact area of the bladder 48 more conforming to the local skin topography.

Desirably, an acoustic coupling medium is also applied between the bladder 48 and the skin surface. The coupling medium can comprise, e.g., a gel material (such as AQUA-SONIC® 100, by Parker Laboratories, Inc., Fairfield, N.J.). The external material can possess sticky or tacky properties, to further enhance the securement of the applicator 18 to the skin.

In the illustrated embodiment, the bladder 48 and bladder chamber 50 together form an integrated part of the applicator 18. Alternatively, the bladder 48 and bladder chamber 50 can be formed by a separate molded component, e.g., a gel or liquid filled pad, which is supplied separately. A molded gel filled pad adaptable to this purpose is the AQUAFLEX® Ultrasound Gel Pad sold by Parker Laboratories (Fairfield, N.J.).

In a representative embodiment, the front mass piece 32 of the acoustic stack 20 measures about 2 inches in diameter, whereas the acoustic contact area formed by the bladder 48 measures about 5 inches in diameter. An applicator 18 that presents an acoustic contact area of larger diameter than the front mass piece 32 of the transducer 40 provides a propagation path for the diverging acoustic beam. Also, a large contact area provides additional stability (with the assembly 12) in hands-free use. In a representative embodiment, the applicator 18 measures about 5 inches in diameter about the bladder 48, about 5 inches in height, and weighs about one pound.

Desirably, when used to apply audible acoustic energy transcutaneously, the diameter of the front mass piece 32 is sized to deliver acoustic energy in a desired range of fundamental frequencies to substantially the entire targeted region. Desirably, the fundamental frequencies lay in a frequency range of about 20 Hz to about 20 kHz, and most desirably, in a range of between 15 kHz and 20 kHz.

Within this range of fundamental frequencies, if the targeted region is, e.g., the thoracic cavity including the heart, the applicator 18 should be sized to percutaneously transmit the energy in a diverging beam, which substantially covers the entire heart and coronary circulation. The applicator 18 may comprise a single transducer or an array of transducers that together form an acoustic contact area.

Normal hearts vary significantly in size and distance from skin between men and women, as well as among individuals regardless of sex. Typically, for men, the size of a normal heart ranges between 8 to 11 cm in diameter and 6 to 9 cm in depth, and the weight ranges between 300 to 350 grams. For men, the distance between the skin and the anterior surface of the heart (which will be called the "subcutaneous depth" of the heart) ranges between 4 to 9 cm. Typically, for women, the size of a normal heart ranges between 7 to 9 cm in diameter and 5 to 8 cm in depth, and the weight ranges between 250 to 300 grams. For women, the subcutaneous depth of the heart ranges between 3 to 7 cm.

The degree of divergence or "directivity" of the acoustic beam transmitted percutaneously through the acoustic contact area is a function of the wavelength of the energy being transmitted. Generally speaking, as the wavelength increases, the beam divergence becomes larger (given a fixed aperture size). If the beam divergence at the subcutaneous depth of the heart is less than beam area of the heart, the audible acoustic energy will not be delivered to substantially the whole heart. Therefore, the beam divergence should desirably be essentially equal to or greater than the targeted beam area at the subcutaneous depth of the heart.

Within the desired range of fundamental frequencies of 20 Hz to 20 kHz, the beam divergence can be expressed in terms of an aperture size measured in wavelengths. The aperture size (AP) can be expressed as a ratio between the effective diameter of the front mass piece 32 (D) and the wavelength of the acoustic energy being applied (WL), or AP=D/WL. The term "effective diameter" is intended to encompass a geometry that is "round," as well as a geometry that is not "round", e.g., being elliptical or rectilinear, but which possesses a surface area in contact with skin that can be equated to an equivalent round geometry of a given effective diameter.

For the desired range of fundamental frequencies of 20 Hz to about 20 kHz, front mass pieces 32 characterized by aperture sizes laying within a range of 0.5 to 5 wavelengths, and preferably less than 2 wavelengths, possess the requisite degree of beam divergence to transcutaneously deliver audible acoustic energy from a position on the thorax, and preferably on or near the sternum, to substantially an entire normal heart of a man or a woman.

Of course, using the same criteria, the transducer face 46 can be suitably sized for other applications within the thoracic cavity or elsewhere in the body. For example, the front mass piece 32 can be sized to delivery energy to beyond the heart and the coronary circulation, to affect the pulmonary circulation.

An O-ring 52 (see FIG. 4) is captured within a groove 54 in the body 38 of the applicator 18 and a groove 84 on the front mass piece 32 of the transducer 40. The O-ring 52 seals the bladder chamber 50 and prevents liquid in the chamber 50 from contacting the sides of the front mass piece 32. Thus, as FIG. 4 shows, only the radiating surface of the front mass piece 32 is in contact with the acoustic coupling medium within the chamber 50.

Desirably, the material of the O-ring 52 is selected to possess elasticity sufficient to allow the acoustic stack 20 of the transducer 40 to vibrate freely in a piston-like fashion within the transducer body 38. Still, the material of the O-ring 52 is selected to be sturdy enough to prevent the acoustic stack 20, while vibrating, from popping out of the grooves 54 and 84.

In a representative embodiment, the O-ring 52 is formed from nitrile rubber (Buna-N) having a hardness of about 30 Shore A to about 100 Shore A. Preferably, the O-ring 52 has a hardness of about 65 Shore A to about 75 Shore A.

Figure 4:
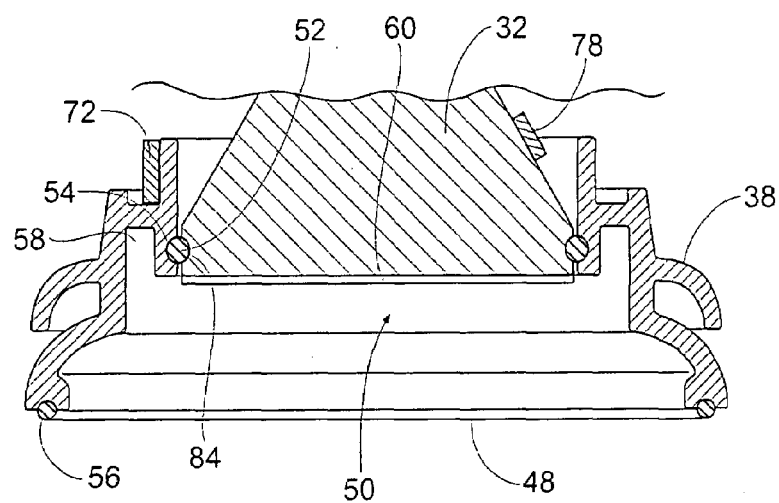
FIG. 4 is a side section view of the acoustic contact area of the audible acoustic energy applicator shown in FIG. 2.

The bladder 48 is stretched across the face of the bladder chamber 50 and is preferably also locked in place with another O-ring 56 (see FIG. 4). A membrane ring may also be used to prevent the O-ring 56 from popping loose. The membrane ring desirably has a layer or layers of soft material (e.g., foam) for contacting the skin.

Localized skin surface heating effects may arise in the presence of air bubbles trapped between the acoustic contact area (i.e., the surface of the bladder 48) and the individual's skin. In the presence of air bubbles acoustic energy may cause cavitation and result in heating at the skin surface. To minimize the collection of air bubbles along the acoustic contact area, the bladder 48 desirably presents a flexible, essentially flat radiating surface contour where it contacts the individual's skin (see FIG. 4), or a flexible, outwardly bowed or convex radiating surface contour (i.e., curved away from the front mass piece) where it contacts with or conducts acoustic energy to the individual's skin. Either a flexible flat or convex surface contour can "mold" evenly to the individual's skin topography, to thereby mediate against the collection and concentration of air bubbles in the contact area where skin contact occurs.

To further mediate against cavitation-caused localized skin surface heating, the interior of the bladder chamber 50 can include a recessed well region 58 surrounding the front mass piece 32. The well region 58 is located at a higher gravity position than the plane of the front mass piece 32. Air bubbles that may form in fluid located in the bladder chamber 50 are led by gravity to collect in the well region 58 away from the acoustic energy beam path.

Figure 7:
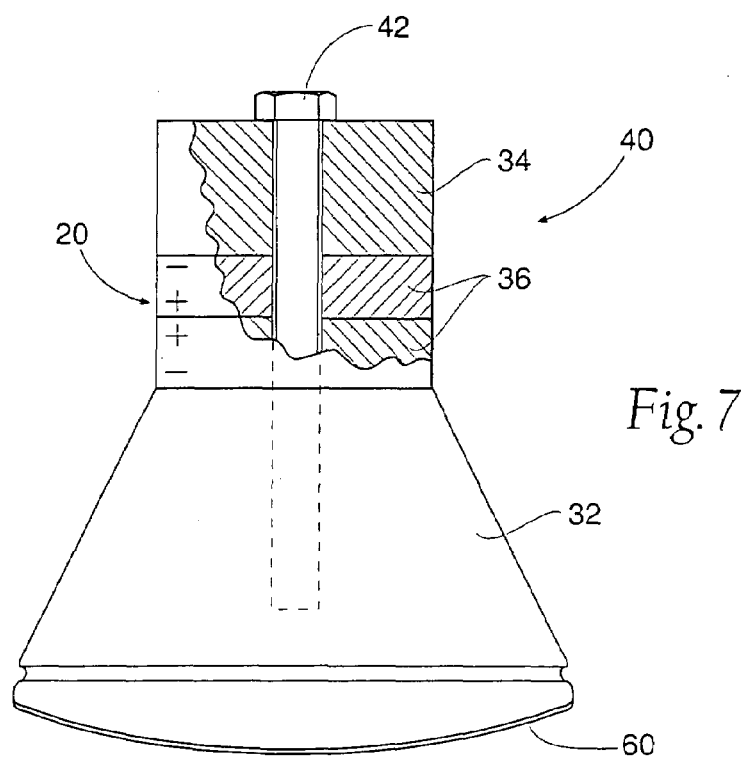
FIG. 7 is a side elevation view, with portions broken away and in section, of an acoustic stack that can be incorporated into the applicator shown in FIG. 2.

The front mass piece 32 desirably possesses either a flat radiating surface (as FIG. 4 shows) or a convex radiating surface (as FIG. 7 shows). The convex radiation surface directs air bubbles off the radiating surface. The radiating surface of the front mass piece may also be coated with a hydrophilic material 60 (see FIG. 4) to prevent air bubbles from sticking.

The transducer 40 may also include a reflux valve/liquid inlet port 62.

The interconnect 30 carries a distal connector 80 (see FIG. 2), designed to easily plug into a mating outlet in the applicator 18. A proximal connector 82 on the interconnect 30 likewise easily plugs into a mating outlet on the chassis 22 (see FIG. 1), which is itself coupled to the controller 26. In this way, the applicator 18 can be quickly connected to the machine 16 at time of use, and likewise quickly disconnected for discard once the treatment session is over. Other quick-connect coupling mechanisms can be used. It should also be appreciated that the interconnect 30 can be hard wired as an integrated component to the applicator 18 with a proximal quick-connector to plug into the chassis 22, or, vice versa, the interconnect 30 can be hard wired as an integrated component to the chassis 22 with a distal quick-connector to plug into the applicator 18.

As FIG. 5 shows, the stabilization assembly 12 allows the operator to temporarily but securely mount the applicator 18 against an exterior skin surface for use. In the illustrated embodiment, since the treatment site exists in the thoracic cavity, the attachment assembly 54 is fashioned to secure the applicator 18 on the person's thorax, overlaying the sternum or breastbone, as FIG. 5 shows.

The assembly 12 can be variously constructed. As shown in FIG. 5, the assembly 12 comprises straps 90 that pass through brackets 92 carried by the applicator 18. The straps 90 encircle the patient's neck and abdomen.

Just as the applicator 18 can be quickly coupled to the machine 16 at time of use, the stabilization assembly 12 also preferably makes the task of securing and removing the applicator 18 on the patient simple and intuitive. Thus, the stabilization assembly 12 makes it possible to secure the applicator 18 quickly and accurately in position on the patient in cramped quarters or while the person (and the system 10 itself) is in transit.

II. Controlling the Application of Audible Acoustic Energy

The system 10 applies audible acoustic energy to achieve vasodilation and/or an increase tissue perfusion without causing substantial deep tissue heating. To achieve the optimal application of audible acoustic energy and this optimal therapeutic effect, the system 10 incorporates selection and tuning of an output frequency. The system 10 can also incorporate other features such as power ramping, output power control, and the application of audible acoustic energy at the selected frequency in pulses.

A. Selection of Output Frequency

Depending upon the treatment parameters and outcome desired, the controller 26 desirably operates a given transducer 40 at a fundamental frequency in the range of about 20 kHz or less. Desirably, the fundamental frequencies lay in a frequency range of about 20 Hz to 20 kHz, and desirably within a range of 15 kHz to 20 kHz.

The applicator 18 can include multiple transducers 40 (or multiple applicators 18 can be employed simultaneously for the same effect), which can be individually conditioned by the controller 26 for operation. One or more transducers 40 within an array of transducers 40 can be operated, e.g., at different fundamental frequencies. For example, one or more transducers 40 can be operated at about 15 kHz, while another one or more transducers 40 can be operated at about 20 kHz. More than two different fundamental frequencies can be used, e.g., about 15 kHz, about 18 kHz, and about 20 kHz.

The controller 26 can trigger the fundamental frequency output according to time or a physiological event (such as ECG or respiration).

Figure 9:
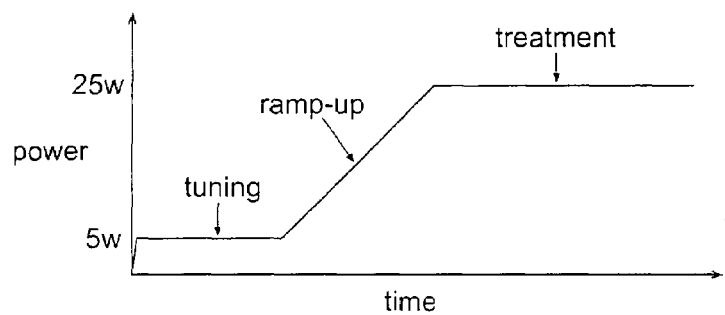
FIG. 9 graphically depicts the technical features of a power ramping function that the system shown in FIG. 1 can incorporate.
Figure 10:
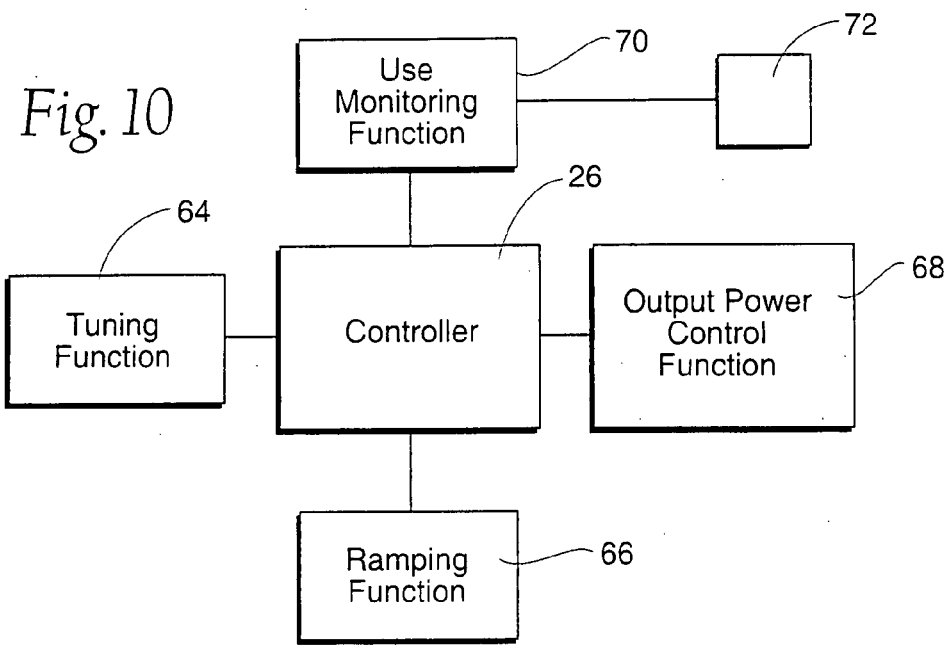
FIG. 10 is a schematic view of a controller that the system shown in FIG. 1 can incorporate, which includes a frequency selection and tuning function, a power ramping function, and an output power control function.

As FIG. 10 shows, the controller 26 desirably includes a tuning function 64. The tuning function 64 selects an optimal frequency at the outset of each treatment session. In the illustrated embodiment (see FIGS. 8A to 8C), the tuning function sweeps the output frequency within a predetermined range of frequencies (f-start to f-stop). The frequency sweep can be and desirably is done at an output power level that is lower than the output power level of treatment (see FIG. 9). The frequency sweep can also be done in either a pulsed or a continuous mode, or in a combination of these two modes. An optimal frequency of operation is selected based upon one or more parameters sensed during the sweeping operation.

Figure 8A:
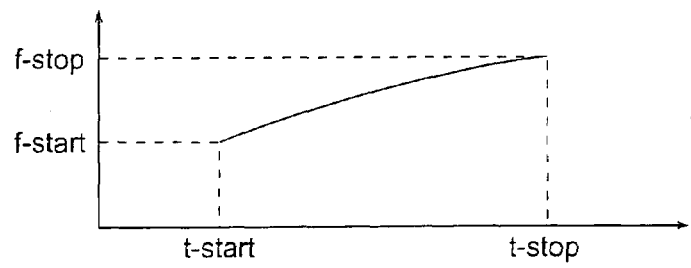
FIG. 8a to 8c graphically depict the technical features of a frequency tuning function that the system shown in FIG. 1 can incorporate.
Figure 8B:
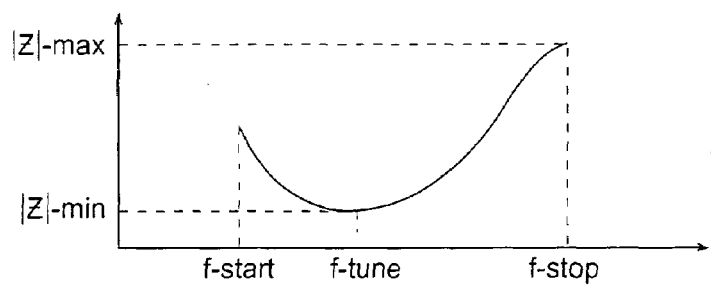
Figure 8C:
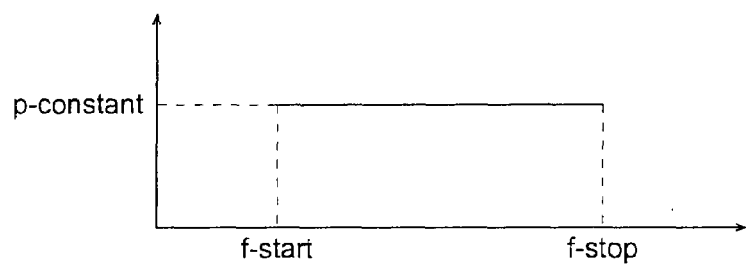

As FIG. 8A shows, the frequency sweep can progress from a lower frequency (f-start) to a higher frequency (f-stop), or vice versa. The sweep can proceed on a linear basis (as FIG. 8A also shows), or it can proceed on a non-linear basis, e.g., logarithmically or exponentially or based upon another mathematical function. The range of the actual frequency sweep may be different from the range that is used to determine the frequency of operation. For instance, the frequency span used for the determination of the frequency of operation may be smaller than the range of the actual sweep range.

In one frequency selection approach (see FIGS. 8A and 8C), while sweeping frequencies, the tuning function 64 adjusts the output voltage and/or current to maintain a constant output power level (p-constant). The function 64 also senses changes in transducer impedance (see FIG. 8B)—Z-min to Z-max—throughout the frequency sweep. In this approach (see FIG. 8B), the tuning function 64 selects as the frequency of operation the frequency (f-tune) where, during the sweep, the minimum magnitude of transducer impedance (Z-min) is sensed. Typically, this is about the same as the frequency of maximum output current (I), which in turn, is about the same as the frequency of minimum output voltage (V).

In an alternative frequency selection approach, the tuning function 64 can select as the frequency of operation the frequency where, during the sweep, the maximum of real part (R) of transducer impedance (Z) occurs, where:

$$|Z|=\sqrt{(R^2+X^2)}$$

and where |Z| is the absolute value of the transducer impedance (Z), which derived according to the following expression:

$$Z=R+iX$$

where R is the real part, and X is the imaginary part.

In another alternative frequency selection approach, while sweeping the frequencies, the tuning function 64 can maintain a constant output voltage. In this approach, the tuning function 64 can select as the frequency of operation the frequency where, during the sweep, the maximum output power occurs. Alternatively, the tuning function 64 can select as the frequency of operation the frequency where, during the sweep, the maximum output current occurs.

B. Power Ramping

As before described, the tuning function 64 desirably operates at an output power level lower than the power level of treatment. In this arrangement, once the operating frequency has been selected, the output power level needs to be increased to the predetermined output level to have the desired therapeutic effect.

In the illustrated embodiment (see FIG. 10), the controller 26 desirably includes a ramping function 66. The ramping function 66 (see FIG. 9) causes a gradual ramp up of the output power level at which the tuning function 64 is conducted (e.g., 5 W) to the power level at which treatment occurs (e.g., 25 W). The gradual ramp up decreases the possibility of unwanted patient reaction to the acoustic exposure. Further, a gradual ramp up is likely to be more comfortable to the patient than the sudden onset of the full output power.

In a desired embodiment, the ramping function 66 increases power at a rate of about 0.01 W/s to about 10 W/s. A particularly desired ramping rate is between about 0.1 W/s to about 5 W/s. The ramping function 66 desirably causes the ramp up in a linear fashion (as FIG. 9 shows). However, the ramping function can employ non-linear ramping schemes, e.g., logarithmic or according to another mathematical function.

C. Output Power Control

Also depending upon the treatment parameters and outcome desired, the controller 26 can operate a given transducer 40 at a prescribed power level, which can remain fixed or can be varied during the treatment session. The controller 26 can also operate one or more transducers 40 within an array of transducers 40 (or when using multiple applicators 18) at different power levels, which can remain fixed or themselves vary over time.

The parameters affecting power output take into account the output of the signal generator module; the physical dimensions and construction of the applicator; and the physiology of the tissue region to which acoustic energy is being applied.

More particularly, the parameters affecting power output can take into account the output of the signal generator module 24; the physical dimensions and construction of the applicator 18; and the physiology of the tissue region to which acoustic energy is being applied. In the context of the illustrated embodiment, these parameters include the total output power ($P_{Total}$) (expressed in watts—W) provided to the transducer 40 by the signal generator module 24; the intensity of the power (expressed in watts per square centimeter—W/cm$^2$) in the effective radiating area of the applicator 18, which takes into account the total power $P_{Total}$ and the area of the bladder 48; and the peak rarefactional acoustic pressure ($P_{Peak(Neg)}$) (expressed in Pascals—Pa) that the tissue experiences, which takes into consideration that the physiological tolerance of tissue to rarefactional pressure conditions is much less than its tolerance to compressional pressure conditions. $P_{Peak(Neg)}$ can be derived as a known function of W/cm$^2$.

In one embodiment, the applicator 18 can be sized to provide an intensity equal to or less than 25 W/cm$^2$ at a maximum total power output of equal to or less than 200 W (most preferably 15 W·$P_{Total}$·150 W) operating at a fundamental frequency of less than or equal to 20 kHz. Audible acoustic energy within the range of fundamental frequencies specified passes through bone, while also providing selectively different mechanical effects (depending upon the frequency), and without substantial deep tissue heating effects, as previously described. Power supplied within the total power output range specified meets the size, capacity, and cost requirements of battery power, to make a transportable, "follow the patient" treatment modality possible, as already described. Audible acoustic energy supplied within the power density range specified keeps peak rarefactional acoustic pressure within physiologically tolerable levels. The applicator 18 meeting these characteristics can therefore be beneficially used in conjunction with the transportable audible energy generator machine 16, as described.

During a given treatment session, the transducer impedance may vary due to a number of reasons, e.g., transducer heating, changes in acoustic coupling between the transducer and patient, and/or changes in transducer bladder fill volume, for instance, due to degassing. In the illustrated embodiment (see FIG. 10), the controller 26 includes an output power control function 68. The output power control function 68 holds the output power constant, despite changes in transducer impedance within a predetermined range. If the transducer falls out of the predetermined range, for instance, due to an open or short circuit, the controller 26 shuts down the generator audible acoustic energy module 24 and desirably sounds an alarm.

Governed by the output power control function 68, as the transducer impedance increases, the output voltage is increased to hold the power output constant. Should the output voltage reach a preset maximum allowable value, the output power will decrease, provided the transducer impedance remains within its predetermined range. As the transducer impedance subsequently drops, the output power will recover, and the full output power level will be reached again.

Governed by the output power control function 68, as the transducer impedance decreases, the output current is increased to hold the power output constant. Should the output current reach a preset maximum allowable value, the output power will decrease until the impedance increases again, and will allow full output power.

In addition to the described changes in the output voltage and current to maintain a constant output power level, the output power control function 68 can vary the frequency of operation slightly upward or downward to maintain the full output power level within the allowable current and voltage limits.

D. Pulsed Power Mode

The application of audible acoustic energy in a pulsed power mode serves, in conjunction with the selection of the fundamental output frequency, to reduce deep heating tissue effects. This is because, at a given frequency, a high acoustic intensity, or high acoustic power, results in more deep heating of tissue than a low intensity, or power. At the same peak acoustic intensity, the pulse mode application of acoustic energy results in less deep heating of tissue than continuous mode because tissue is cooled off in between the pulses. During the pulsed power mode, audible acoustic energy is applied at a desired fundamental frequency or within a desired range of fundamental frequencies at the prescribed power level or range of power levels (as described above, to achieve the desired physiological effect) in a prescribed duty cycle (DC) (or range of duty cycles) and a prescribed pulse repetition frequency (PRF) (or range of pulse repetition frequencies). Desirably, the pulse repetition frequency (PRF) is between about 20 Hz to about 50 Hz (i.e., between about 20 pulses a second to about 50 pulses a second).

The duty cycle (DC) is equal to the pulse duration (PD) divided by one over the pulse repetition frequency (PRF). The pulse duration (PD) is the amount of time for one pulse. The pulse repetition frequency (PRF) represents the amount of time from the beginning of one pulse to the beginning of the next pulse. For example, given a pulse repetition frequency (PRF) of 30 Hz (30 pulses per second) and a duty cycle of 25% yields a pulse duration (PD) of approximately 8 ms pulse followed by a 25 ms off period 30 times per second.

Given a pulse repetition frequency (PRF) selected at 25 Hz and a desired fundamental frequency between about 15 kHz and 20 kHz delivered in a power range between about 5 to 30 W, a duty cycle of about 50% or less meets the desired physiological objectives with less incidence of localized conductive heating effects compared to a continuous application of the same fundamental frequency and power levels over a comparable period of time. Given these operating conditions, the duty cycle desirably lays in a range of between about 1% and about 35%.

III. Monitoring Use of the Transducer

To protect patients from the potential adverse consequences occasioned by multiple use, which include disease transmission, or material stress and instability, or decreased or unpredictable performance, the controller 26 desirably includes a use monitoring function 70 (see FIG. 10) that monitors incidence of use of a given transducer 40.

In the illustrated embodiment, the transducer 40 carries a use register 72 (see FIG. 4). The use register 72 is configured to record information before, during, and after a given treatment session. The use register 72 can comprise a solid state micro-chip, ROM, EEPROM, EPROM, or non volatile RAM (NVRAM) carried by the transducer 40.

Figure 11:
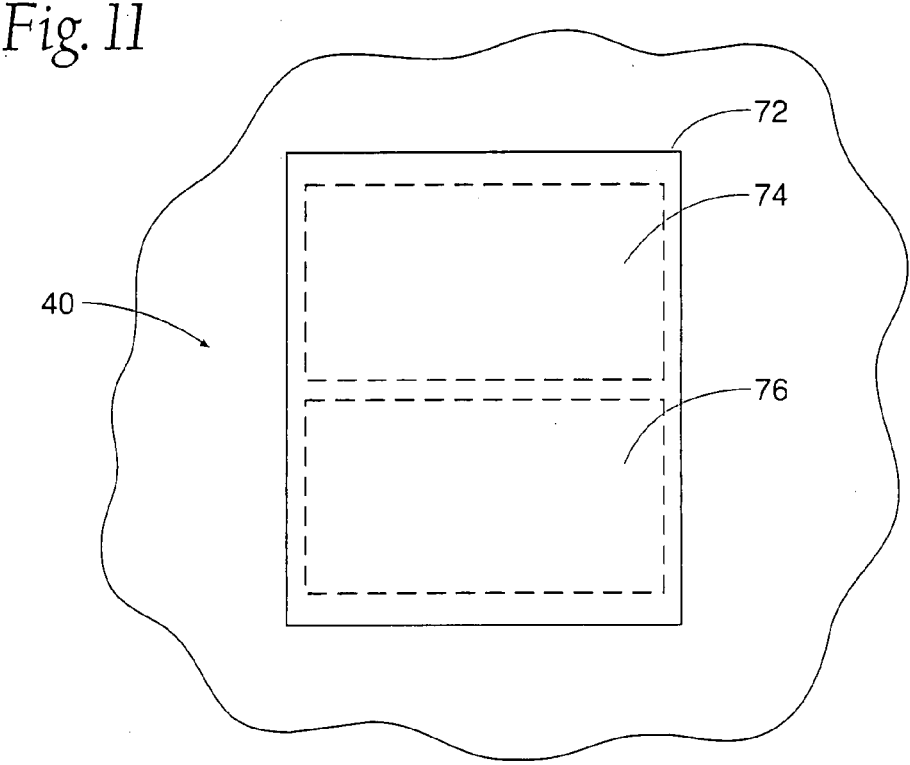
FIG. 11 is a diagrammatic view of a use register chip that forms a part of the use monitoring function shown in FIG. 10.

The use register 72 is initially formatted and programmed by the manufacturer of the system to include memory fields. In the illustrated embodiment (see FIG. 11), the memory fields of the use register are of two general types: Write Many Memory Fields 74 and Write-Once Memory Fields 76. The Write Many Memory Fields 74 record information that can be changed during use of the transducer 40. The Write-Once Memory Fields 76 record information that, once recorded, cannot be altered.

The specific information recorded by the Memory Fields 74 and 76 can vary. The following table exemplifies typical types of information that can be recorded in the Write Many Memory Fields 74.

| Field Name | Description | Location | Size (Byte) |
|---|---|---|---|
| Treatment Complete | If a transducer has been used for a prescribed maximum treatment time (e.g., 60 minutes), the treatment complete flag is set to 1 otherwise it is zero. | 0 | 1 |
| Prescribed Maximum Treatment Time (Minutes) | This is the allowable usage time of the transducer. This is set by the manufacturer and determines at what point the Treatment Complete flag is set to 1. | 1–2 | 2 |
| Elapsed Usage Time (Minutes) | Initialized to zero. This area is then incremented every minute that the system is transmitting acoustic energy. This area keeps track of the amount of time that the transducer has been used. When this | 3–4 | 2 |

-continued

| Field Name | Description | Location | Size (Byte) |
|---|---|---|---|
| | time reaches the Prescribed Maximum Treatment Time, the Treatment Complete flag is set to 1. | | |
| Transducer Frequency | This is an area that could be used to prescribe the operational frequency of the transducer, rather than tuning the transducer to an optimal frequency, as above described. In the latter instance, this area shows the tuned frequency once the transducer has been tuned. | 5–6 | 2 |
| Average Power (Watts) | The system reads and accumulates the delivered power throughout the procedure. Every minute, the average power number is updated in this area from the system, at the same time the Elapsed Usage Time is updated. when the Usage time clock is updated. This means that the average power reading could be off by a maximum of 59 seconds if the treatment is stopped before the Treatment Complete flag is set. This average power can be used as a check to make sure that the system was running at full power during the procedure. | 7–8 | 2 |
| Applicator CRC | Use Register CRC. This desirably uses the same CRC algorithm used to protect the controller ROM. | 9–10 | 2 |
| Copyright Notice | Desirably, the name of the manufacturer is recorded in this area. Other information can be recorded here as well. | 11–23 | 11 |

The on/off cycles of acoustic energy transmission could affect the accuracy of the recorded power levels because of the variance of the power levels due to ramping function 66. For this reason it may be advantageous to also record the number of on/off cycles of acoustic energy transmission. This will help explain any discrepancies in the average power reading. It might also allow the identification of procedural problems with system use.

Each use register 72 can be assigned a unique serial number that could be used to track transducers in the field. This number can be read by the use monitoring function 70 if desired.

The following table exemplifies typical types of information that can be recorded in the Write-Once Memory Fields 76.

| Field Name | Description | Location | Size (Byte) |
|---|---|---|---|
| Treatment Complete | If a transducer has been used for a prescribed maximum treatment time (e.g., 60 minutes), the treatment complete flag is set to 1 otherwise it is zero. | 0 | 1 |
| Prescribed Maximum Treatment Time (Minutes) | This is the allowable usage time of the transducer. This is set by the manufacturer and determines at what point the Treatment Complete flag is set to 1. | 1–2 | 2 |
| Elapsed Usage Time (Minutes) | Initialized to zero. This area is then incremented every minute that the system is transmitting acoustic energy. This area keeps track of the amount of time that the transducer has been used. When this time reaches the Prescribed Maximum Treatment Time, the Treatment Complete flag is set to 1. | 3–4 | 2 |
| Transducer Frequency | This is an area that could be used to prescribe the operational frequency of the transducer, rather than tuning the transducer to an optimal frequency, as above described. In the latter instance, this area shows the tuned frequency once the transducer has been tuned. | 5–6 | 2 |
| Average Power (Watts) | The system reads and accumulates the delivered power throughout the procedure. Every minute, the average power number is updated in this area from the system, at the same time the Elapsed Usage Time is updated. When the Usage time clock is updated. This means that the average power reading could be off by a maximum of 59 seconds if the treatment is stopped before the Treatment Complete flag is set. This average power can be used as a check to make sure that the system was running at full power during the procedure. | 7–8 | 2 |
| Applicator CRC | Use Register CRC. This desirably uses the same CRC algorithm used to protect the controller ROM. | 9–10 | 2 |
| Copyright Notice | Desirably, the name of the manufacturer is recorded in this area. Other information can be recorded here as well. | 11–23 | 11 |

The on/off cycles of acoustic energy transmission could affect the accuracy of the recorded power levels because of the variance of the power levels due to ramping function 66. For this reason it may be advantageous to also record the number of on/off cycles of acoustic energy transmission. This will help explain any discrepancies in the average power reading. It might also allow the identification of procedural problems with system use.

Each use register 72 can be assigned a unique serial number that could be used to track transducers in the field. This number can be read by the use monitoring function 70 if desired.

The following table exemplifies typical types of information that can be recorded in the Write-Once Memory Fields 76.

| Field Name | Description | Size (Bytes) |
|---|---|---|
| Start Date Time | Once the system has tuned the transducer and started to transmit acoustic energy, the current date and time are written to this area. This area is then locked, which prevents the data from ever-being changed. | |
| Tuned Frequency | The tuned frequency is written to this location when the Start Date and Time is set. This prevents this information from being written over on subsequent tunes (if necessary). | |

Figure 12:
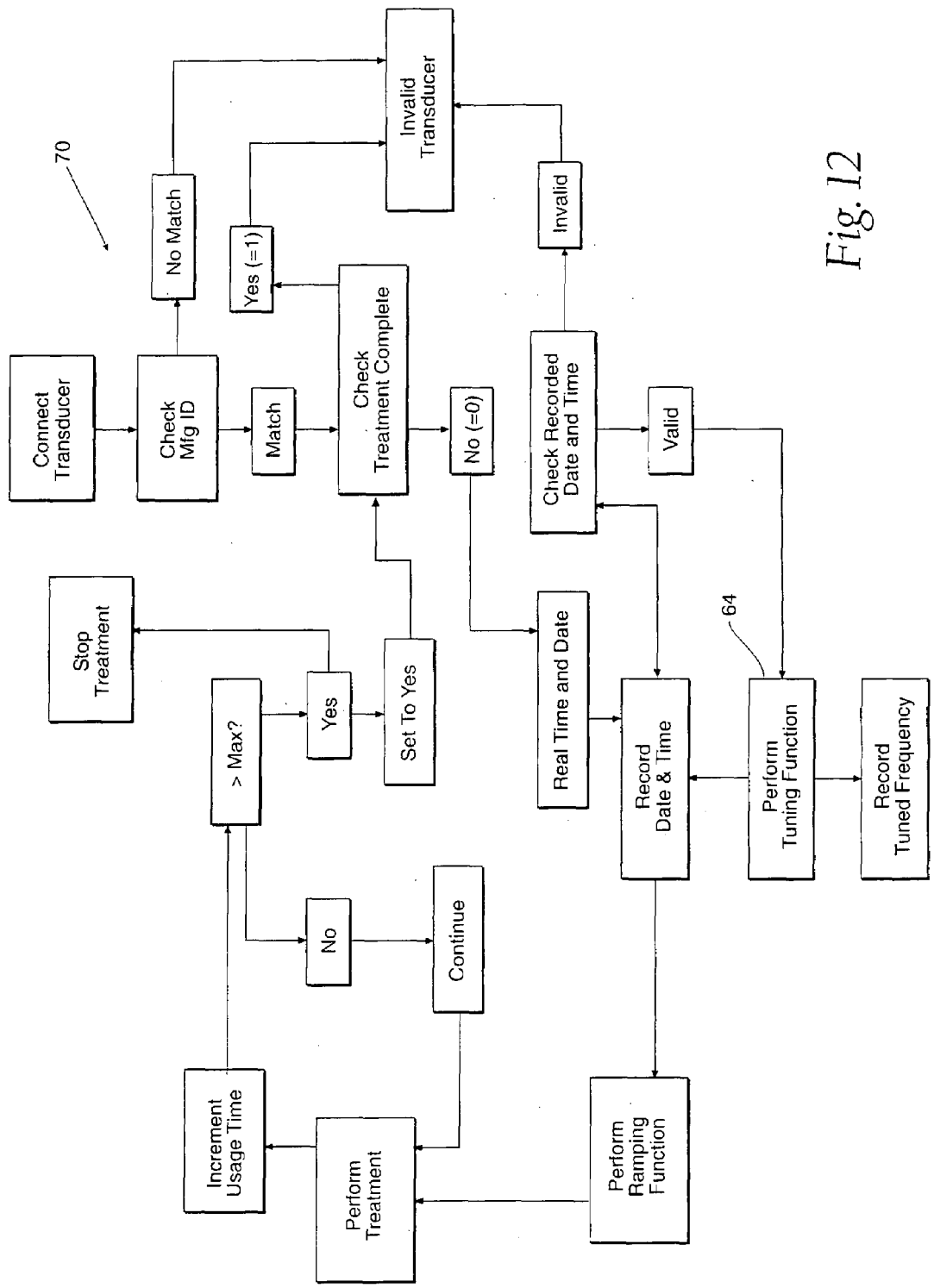
FIG. 12 is a diagrammatic flow chart showing the technical features of the use monitoring function shown in FIG. 10.

As FIG. 12 shows, when a transducer 40 is first coupled to the machine 16, and prior to enabling the conveyance of audible acoustic energy to the transducer 40, the use monitoring function 70 prompts the use register 72 to output resident information recorded in the memory fields.

The use monitoring function 70 compares the contents of the Copyright Notice field to a prescribed content. In the illustrated embodiment, the prescribed content includes information contained in the Copyright Notice field of the Write Many Memory Fields 74. The prescribed content therefore includes the name of the manufacturer, or other indicia uniquely associated with the manufacture. If the prescribed content is missing, the use monitoring function 70 does not enable use of the transducer 40, regardless of the contents of any other memory field. The transducer 40 is deemed "invalid." In this way, a manufacturer can assure that only transducers meeting its design and quality control standards are operated in association with the machine 16.

If the contents of the Copyright Notice field match, the use monitoring function 70 compares the digital value residing in the Treatment Complete field of the Write Many Memory Fields 74 to a set value that corresponds to a period of no prior use or a prior use less than the Prescribed Maximum Treatment Time—i.e., in the illustrated embodiment, a zero value. A different value (i.e., a 1 value) in this field indicates a period of prior use equal to or greater than the Prescribed Maximum Treatment Time. In this event, the use monitoring function 70 does not enable use of the transducer 40. The transducer 40 is deemed "invalid."

If a value of zero resides in the Treatment Complete field, the use monitoring function 70 compares the date and time data residing in the Write-Once Start Date and Time field to the current date and time established by a Real Time Clock. If the Start Date and Time is more than a prescribed time before the Real Time (e.g., 4 hours), the controller does not enable use of the transducer 40. The transducer 40 is deemed "invalid."

If the Start Date and Time field is empty, or if it is less than the prescribed time before the Real Time, the use monitoring function 70 deems the transducer 40 to be "valid" (providing the preceding other criteria have been met). The use monitoring function 70 reports a valid transducer to the controller 26, which initiates the tuning function 64. If the Start Date and Time field is empty, once the tuning function 64 is completed, the controller prompts the use monitoring function 70 to records the current date and time in the Start Date and Time Field, as well as the selected operating frequency in the Tuned Frequency field. The controller 26 then proceeds to execute the ramping function 66 and, then, execute the prescribed treatment protocol.

If the Start Date and Time field is not empty (indicating a permitted prior use), once the tuning function 64 is completed, the controller 26 immediately proceeds with the ramping function 66 and, then, execute the treatment protocol.

During use of the transducer 40 to accomplish the treatment protocol, the use monitoring function 70 periodically updates the Elapsed Usage Time field and Average Power field (along with other Many Write Memory Fields). Once the Treatment Complete flag is set to a 1 value (indicating use of the transducer beyond the Prescribed Maximum Treatment Time), the use monitoring function 70 interrupts the supply of energy to the transducer. The transducer 40 is deemed "invalid" for subsequent use. The use monitoring function 70 can also generate an output that results in a visual or audible alarm, informing the operator that the transducer 40 cannot be used.

The information recorded in the use register 72 can also be outputted to monitor use and performance of a given transducer 40. Other sensors can be used, e.g., a temperature sensor 78 carried on the front mass piece 32 (see FIG. 4), in association with the use register.

As described, the use register 72 allows specific pieces of information to be recorded before, during and after a treatment is complete. Information contained in the use register 72 is checked before allowing use of a given transducer 40. The use register 72 ensures that only a transducer 40 having the desired design and performance criteria imparted by the manufacturer can be used. In addition, the use register 72 can be used to "lock out" a transducer 40 and prevent it from being used in the future. The only way the transducer 40 could be reused is to replace the use register 72 itself. However, copying the architecture of the use register 72 (including the contents of the Copyright Message field required for validation) itself constitutes a violation of the manufacturer's copyright in a direct and inescapable way.

IV. Use with a Therapeutic Agent

The system 10 can be further include at the treatment location a delivery system for introducing a therapeutic agent in conjunction with the use of the applicator 18 and machine 16. In this arrangement, the effect of vasodilation and/or increased tissue perfusion caused by the application of audible acoustic energy can also be enhanced by the therapeutic effect of the agent, or vice versa.

A. Use with a Thrombolytic Agent

For example, the therapeutic agent can comprise a thrombolytic agent. In this instance, the thrombolytic agent is introduced into a thrombosis site, prior to, in conjunction with, or after the application of audible acoustic energy. The interaction between the applied audible acoustic energy and the thrombolytic agent is observed to assist in the breakdown or dissolution of the trombi, compared with the use of the thrombolytic agent in the absence of audible acoustic energy. This phenomenon is discussed, e.g., in Carter U.S. Pat. No. 5,509,896; Siegel et al U.S. Pat. No. 5,695,460; and Lauer et al U.S. Pat. No. 5,399,158, which are each incorporated herein by reference.

The process by which thrombolysis is affected by use of audible acoustic energy in conjunction with a thrombolytic agent can vary according to the frequency, power, and type of acoustic energy applied, as well as the type and dosage of the thrombolytic agent. The application of acoustic energy has been shown to cause reversible changes to the fibrin structure within the thrombus, increased fluid dispersion into the thrombus, and facilitated enzyme kinetics. These mechanical effects beneficially enhance the rate of dissolution of thrombi. In addition, cavitational disruption, acoustic radiation pressure and streaming effects can also assist in the breakdown and dissolution of thrombi.

The type of thrombolytic agent used can vary. The thrombolytic agent can comprise a drug known to have a thrombolytic effect, such as t-PA, TNKase, or RETAVASE. Alternatively (or in combination), the agent can comprise an anticoagulant, such as heparin; or an antiplatelet drug, such as GP IIb IIIa inhibitor; or a fibrinolytic drug; or a non-prescription agent having a known beneficial effect, such as aspirin. Alternatively (or in combination), the thrombolytic agent can comprise microbubbles, which can be acoustically activated; or microparticles, which contain albumin.

The syndrome being treated can also vary, according to the region of the body. For example, in the thoracic cavity, the thrombolytic syndrome can comprise acute myocardial infarction, or acute coronary syndrome. The syndrome can alternatively comprise suspect myocardial ischemia, prinzmetal angina, chronic angina, or pulmonary embolism.

The thrombolytic agent is typically administered by a delivery system intravenously prior to or during the application of acoustic energy. The dosage of the thrombolytic agent is determined by the physician according to established treatment protocols.

It may be possible to reduce the typical dose of thrombolytic agent when acoustic energy is also applied. It also may be possible to use a less expensive thrombolytic agent or a less potent thrombolytic agent when acoustic energy is applied. The ability to reduce the dosage of thrombolytic agent, or to otherwise reduce the expense of thrombolytic agent, or to reduce the potency of thrombolytic agent, when audible acoustic energy is also applied, can lead to additional benefits, such as decreased complication rate, an increased patient population eligible for the treatment, and increased locations where the treatment can be administered (i.e., outside hospitals and critical care settings, as well as in private, in-home settings).

B. Use with an Angiogenic Agent

Treatment using audible acoustic energy alone can simulate additional capillary or microcirculatory activity, resulting in an arteriogenesis/angiogenesis effect. This treatment can be used as an adjunct to treatment using angiogenic agents released in the coronary circulation to promote new arterial or venous growth in ischemic cardiac tissue or elsewhere in the body. In this instance, the therapeutic agent can comprise an angiogenic agent, e.g., Monocyte Chemoattractant Protein-1, or Granulocyte-Macrophage Colony-Stimulating-Factor.

It is believed that the angiogenic effects of these agents can be enhanced by shear-related phenomena associated with increased blood flow through the affected area. Increased blood perfusion in the heart caused by the application of audible acoustic energy can induce these shear-related phenomena in the presence of the angiogenic agents, and thereby lead to increased arterial-genesis and/or vascular-genesis in ischematic heart tissue.

C. Use of the System with Other Treatment Applications

The system 10 can be used to carry out other therapeutic treatment objectives, as well.

For example, the system 10 can be used to carry out cardiac rehabilitation. The repeated application of audible acoustic energy over an extended treatment period can exercise and strengthen heart muscle weakened by disease or damage. As another example, treatment using audible acoustic energy can facilitate an improvement in heart wall motion or function.

The system 10 may also be used in association with other diagnostic or therapeutic modalities to achieve regional systemic therapy. For example, a first selected treatment modality can be applied to the body to achieve a desired systemic effect (for example, the restriction of blood flow). A second selected treatment modality, which comprises the audible acoustic energy delivery system 10 previously described, can also be applied before, during, or after the first treatment modality, at least for a period of time, to transcutaneously apply acoustic energy to a selected localized region of the body (e.g., the thoracic cavity) to achieve a different, and perhaps opposite, localized system result, e.g., increased tissue perfusion.

For example, an individual who has received a drug that systemically decreases blood flow or blood pressure may experience a need for increased blood perfusion to the heart, e.g., upon experiencing a heart attack. In this situation, the audible acoustic energy delivery system 10 can be used to locally apply audible acoustic energy to the thoracic cavity, to thereby locally increase blood perfusion to and in the heart, while systematic blood perfusion remains otherwise lowered outside the region of the heart due to the presence of the drug in the circulatory system of the individual.

As another example, this demonstrating the ability of locally applied acoustic energy to increase drug uptake, a chemotherapy drug may be systemically or locally delivered (by injection or by catheter) to an individual. The audible acoustic energy delivery system 10 can be used to locally supply audible acoustic energy to the targeted region, where the tumor is, to locally increase perfusion or uptake of the drug.

The purposeful design of the durable and disposable equipment of the system 10 makes it possible to carry out these therapeutic protocols outside a traditional medical setting, such as in a person's home.

Various features of the invention are set forth in the following claims.

We claim:

1. A system for applying audible acoustic energy to a targeted body region cause vasodilation and/or to increase tissue perfusion comprising
   an audible acoustic energy applicator sized to be placed in acoustic contact with the individual to transcutaneously apply audible acoustic energy to the targeted body region, the audible acoustic energy applicator comprising a transducer including a radiating surface, an acoustic coupling media for the transducer, and a well region surrounding the radiating surface and being located at a higher plane than the radiating surface to collect air bubbles forming in the acoustic coupling media, and
   an electrical signal generating machine adapted to be coupled to the audible acoustic energy applicator, the electrical signal generating machine including a controller to generate electrical signals to operate the audible acoustic energy applicator during a treatment session to produce audible acoustic energy.

2. A system according to claim 1
   wherein the controller generates audible acoustic energy at a fundamental frequency laying within a range of fundamental frequencies not greater than about 20 kHz.

3. A system according to claim 2
   wherein the range of fundamental frequencies is between about 20 Hz and 20 kHz.

4. A system according to claim 2
   wherein the fundamental frequency is between 15 kHz and 20 kHz.

5. A system according to claim 1
   wherein the audible acoustic energy applicator is sized to provide an intensity not exceeding 25 watts/cm2 at a maximum total power output of no greater than 150 watts operating within a range of fundamental frequencies not greater than 20 kHz.

6. A system according to claim 5 wherein the range of fundamental frequencies is between about 20 Hz and 20 kHz.

7. A system according to claim 5 wherein the fundamental frequency is between 15 kHz and 20 kHz.

8. A system according to claim 1 wherein the transducer includes an acoustic coupling region having an effective diameter (D) to transcutaneously apply audible acoustic energy at a prescribed fundamental frequency, the transducer having an aperture size (AP) not greater than about 5 wavelengths, wherein AP is expressed as AP=D/WL, where WL is the wavelength of the fundamental frequency.

9. A system according to claim 8 wherein the controller generates audible acoustic energy at a fundamental frequency laying within a range of fundamental frequencies not greater than 20 kHz.

10. A system according to claim 9 wherein the range of fundamental frequencies is between about 20 Hz and 20 kHz.

11. A system according to claim 9 wherein the range of fundamental frequencies is between 15 kHz and 20 kHz.

12. A system according to claim 1 further including an assembly sized and configured to be affixed to the audible acoustic energy applicator and worn by the individual to stabilize placement of the audible acoustic energy applicator on the individual during transcutaneous application of audible acoustic energy.

13. A system according to claim 1 wherein the audible acoustic energy applicator comprises an acoustic coupling region for the transducer that includes a flexible material that forms a contour-conforming interface with skin.

14. A system according to claim 13 wherein the flexible material presents a generally flat surface for contact with skin.

15. A system according to claim 13 wherein the flexible material presents a generally convex surface for contact with skin.

16. A system according to claim 1 wherein the radiating surface has a radiating surface area, wherein the audible acoustic energy applicator comprises an acoustic coupling region for the transducer, the acoustic coupling region having a surface area that is larger than the radiating surface area.

17. A system according to claim 1 wherein the audible acoustic energy applicator comprises an acoustic coupling region for the transducer spaced from the radiating surface to space the radiating surface from contact with skin.

18. A system according to claim 1 wherein the radiating surface is generally flat.

19. A system according to claim 18 wherein the radiating surface includes a hydrophilic coating.

20. A system according to claim 1 wherein the radiating surface is generally convex.

21. A system according to claim 20 wherein the radiating surface includes a hydrophilic coating.

22. A system according to claim 1 wherein the radiating surface is generally convex to direct air bubbles toward the well region.

23. A system according to claim 1 wherein the radiating surface includes a hydrophilic coating to shed air bubbles.

24. A system according to claim 1 further including a use register sized and configured to be carried by the audible acoustic energy applicator, and wherein the controller includes a use monitoring function adapted and configured to be coupled to the use register and an enablement function that enables operation of the audible acoustic energy applicator when prescribed use criteria are satisfied.

25. A system according to claim 1 wherein the controller is adapted and configured to execute a tuning function that delivers audible acoustic energy to the audible acoustic energy applicator at an output frequency that varies over time within a range of output frequencies and selects from within the range an operating output frequency for the audible acoustic energy applicator based upon preprogrammed selection rules.

26. A system according to claim 1 wherein the controller generates electrical signals to operate the audible acoustic energy applicator in pulses.

27. A system according to claim 1 wherein the electrical signal generating machine is sized and configured to apply audible acoustic energy to the individual while the individual is undergoing transport.

28. A method for treating an acute coronary syndrome comprising the step of using the system defined in claim 1 to apply audible acoustic energy to a targeted body region to cause vasodilation and/or increase tissue perfusion.

29. A method for treating a heart attack comprising the step of using the system defined in claim 1 to apply audible acoustic energy to a targeted body region to cause vasodilation and/or increase tissue perfusion.

30. A method for treating stroke comprising the step of using the system defined in claim 1 to apply audible acoustic energy to a targeted body region to cause vasodilation and/or increase tissue perfusion.

31. A method for treating vascular disease comprising the step of using the system defined in claim 1 to apply audible acoustic energy to a targeted body region to cause vasodilation and/or increase tissue perfusion.

32. A method for increasing drug uptake comprising the step of using the system defined in claim 1 to apply audible acoustic energy to a targeted body region to cause vasodilation and/or increase tissue perfusion.

33. A method comprising the step of using the system defined in claim 1 to apply audible acoustic energy to a targeted body region to cause vasodilation and/or increase tissue perfusion.

34. A method for achieving regional systemic therapy in an individual comprising the steps of
administering an agent to the individual, and
using the system defined in claim 1 to apply audible acoustic energy to a targeted body region to cause vasodilation and/or increase tissue perfusion to affect an increase in uptake of the agent in the targeted body region before, during or after administration of the agent to the individual.

35. A method according to claim 34 wherein the agent in an angiogenic material.

* * * * *